United States Patent
Smith

(10) Patent No.: US 9,144,422 B2
(45) Date of Patent: Sep. 29, 2015

(54) SURGICAL ACCESS ASSEMBLY AND METHOD OF USE THEREFOR

(71) Applicant: Covidien LP, Mansfield, MA (US)

(72) Inventor: Robert C. Smith, Middlefield, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/498,139

(22) Filed: Sep. 26, 2014

(65) Prior Publication Data

US 2015/0011835 A1 Jan. 8, 2015

Related U.S. Application Data

(63) Continuation of application No. 13/650,162, filed on Oct. 12, 2012, now Pat. No. 8,845,529.

(60) Provisional application No. 61/581,197, filed on Dec. 29, 2011.

(51) Int. Cl.
*A61B 1/32* (2006.01)
*A61B 17/02* (2006.01)
(Continued)

(52) U.S. Cl.
CPC ............. *A61B 17/0218* (2013.01); *A61B 1/32* (2013.01); *A61B 17/3423* (2013.01); *A61B 17/3431* (2013.01); *A61B 17/0293* (2013.01); *A61B 2017/00265* (2013.01); *A61B 2017/0225* (2013.01); *A61B 2017/3429* (2013.01); *A61B 2017/3445* (2013.01)

(58) Field of Classification Search
CPC ........... A61B 1/32; A61B 2017/00265; A61B 17/0218; A61B 2017/0225; A61B 17/0293; A61B 17/3423; A61B 2017/3429; A61B 17/3431; A61B 2017/3445
USPC ................................. 606/201, 206–208, 210
See application file for complete search history.

(56) References Cited

U.S. PATENT DOCUMENTS 4,984,564 A 1/1991 Yuen
5,366,478 A 11/1994 Brinkerhoff et al.
(Continued)

FOREIGN PATENT DOCUMENTS

EP 2238926 A2 10/2010
EP 2238933 A1 10/2010
WO 2010/141409 12/2010

OTHER PUBLICATIONS

European Search Report dated Apr. 24, 2013 from European Application No. 12198750.7. (4 pgs.).

*Primary Examiner* — Larry E Waggle, Jr.

(57) ABSTRACT

A surgical access assembly includes an access port, a seal anchor and a sealing adapter. The access port includes proximal and distal rings and a sleeve defining a passage therethrough. The sleeve extends between the proximal and distal rings. The seal anchor is adapted to be at least partially disposed in the access port. The sealing adapter includes proximal and distal end portions. The distal end portion is configured and dimensioned to engage the seal anchor in a sealing relation therewith. The proximal end portion is configured and dimensioned to engage a least a portion of the distal ring of the access port in a sealing relation therewith, wherein the sealing adapter is transitionable between a first state in which the sealing adapter has a first diameter and a second state in which the sealing adapter has a second diameter. The second diameter is larger than the first diameter.

5 Claims, 16 Drawing Sheets

(51) Int. Cl.
 *A61B 17/34* (2006.01)
 *A61B 17/00* (2006.01)

(56) References Cited

U.S. PATENT DOCUMENTS

| | | | |
|---|---|---|---|
| 5,524,644 A | 6/1996 | Crook | |
| 5,735,791 A | 4/1998 | Alexander, Jr. et al. | |
| 5,741,298 A | 4/1998 | MacLeod | |
| 5,803,921 A | 9/1998 | Bonadio | |
| 6,033,426 A | 3/2000 | Kaji | |
| 6,142,936 A | 11/2000 | Beane et al. | |
| 6,254,534 B1 | 7/2001 | Butler et al. | |
| 6,450,983 B1 | 9/2002 | Rambo | |
| 6,558,371 B2 | 5/2003 | Dorn | |
| 6,582,364 B2 | 6/2003 | Butler et al. | |
| 6,623,426 B2 | 9/2003 | Bonadio et al. | |
| 6,723,044 B2 | 4/2004 | Pulford et al. | |
| 7,033,319 B2 | 4/2006 | Pulford et al. | |
| 7,081,089 B2 | 7/2006 | Bonadio et al. | |
| 7,153,261 B2 | 12/2006 | Wenchell | |
| 7,195,590 B2 | 3/2007 | Butler et al. | |
| 7,377,898 B2 | 5/2008 | Ewers et al. | |
| 7,445,597 B2 | 11/2008 | Butler et al. | |
| 7,473,221 B2 | 1/2009 | Ewers et al. | |
| 7,559,893 B2 | 7/2009 | Bonadio et al. | |
| 7,650,887 B2 | 1/2010 | Nguyen et al. | |
| 7,704,207 B2 | 4/2010 | Albrecht et al. | |
| 7,727,146 B2 | 6/2010 | Albrecht et al. | |
| 7,736,306 B2 | 6/2010 | Brustad et al. | |
| 7,909,760 B2 | 3/2011 | Albrecht et al. | |
| 7,998,068 B2 | 8/2011 | Bonadio et al. | |
| 8,021,296 B2 | 9/2011 | Bonadio et al. | |
| 8,142,354 B1 * | 3/2012 | Larson et al. | 600/203 |
| 8,845,529 B2 * | 9/2014 | Smith | 600/208 |
| 2001/0037053 A1 | 11/2001 | Bonadio et al. | |
| 2004/0267096 A1 | 12/2004 | Caldwell et al. | |
| 2005/0020884 A1 | 1/2005 | Hart et al. | |
| 2005/0148823 A1 | 7/2005 | Vaugh et al. | |
| 2005/0192483 A1 | 9/2005 | Bonadio et al. | |
| 2005/0203346 A1 | 9/2005 | Bonadio et al. | |
| 2006/0161049 A1 | 7/2006 | Beane et al. | |
| 2006/0161050 A1 | 7/2006 | Butler et al. | |
| 2006/0247498 A1 | 11/2006 | Bonadio et al. | |
| 2007/0093695 A1 | 4/2007 | Bonadio et al. | |
| 2007/0203398 A1 | 8/2007 | Bonadio et al. | |
| 2008/0097162 A1 | 4/2008 | Bonadio et al. | |
| 2008/0200767 A1 | 8/2008 | Ewers et al. | |
| 2010/0249516 A1 | 9/2010 | Shelton, IV et al. | |
| 2010/0249525 A1 * | 9/2010 | Shelton et al. | 600/208 |
| 2011/0066001 A1 * | 3/2011 | Shelton et al. | 600/208 |
| 2011/0251463 A1 | 10/2011 | Kleyman | |
| 2011/0251464 A1 | 10/2011 | Kleyman | |
| 2012/0130177 A1 | 5/2012 | Davis | |
| 2012/0130186 A1 | 5/2012 | Stopek et al. | |
| 2012/0130187 A1 | 5/2012 | Okoniewski | |
| 2012/0157779 A1 | 6/2012 | Fischvogt | |
| 2012/0157781 A1 | 6/2012 | Kleyman | |
| 2012/0157786 A1 | 6/2012 | Pribanic | |
| 2012/0190933 A1 | 7/2012 | Kleyman | |
| 2012/0253134 A1 * | 10/2012 | Smith | 600/203 |

* cited by examiner

SURGICAL ACCESS ASSEMBLY AND METHOD OF USE THEREFOR

CROSS REFERENCE TO RELATED APPLICATION

The present application is a continuation of U.S. patent application Ser. No. 13/650,162, filed on Oct. 12, 2012, which claims the benefit of and priority to U.S. Provisional Application Ser. No. 61/581,197, filed on Dec. 29, 2011, the entire contents of which are incorporated herein by reference.

BACKGROUND

1. Technical Field

The present disclosure relates to a surgical access assembly, and more particularly, to a surgical access assembly including an access port and a seal anchor adaptably engaging each other in a sealing relation and a method of use therefor.

2. Background of Related Art

Various surgical procedures are performed in a minimally invasive manner. This includes forming a small opening through a body wall of the patient, e.g., in the abdomen, and inserting a seal anchor through the opening to provide a substantially fluid-tight seal between a body cavity of a patient and the atmosphere. Due to the relatively small interior dimensions of the access devices used in endoscopic procedures, only the elongated, small diametered instrumentation such as, e.g., trocar and cannula assemblies, may be used to access the internal body cavities and organs. In general, prior to the introduction of the surgical object into the patient's body, insufflation gases are used to enlarge the area surrounding the target surgical site to create a larger, more accessible work area.

When compared to the larger openings typically found in traditional procedures, both trauma to the patient and recovery time are reduced for procedures involving small openings. However, minimally invasive surgery such as, e.g., laparoscopy, has several limitations. In particular, surgery of this type requires a great deal of skill in manipulating the long narrow endoscopic instruments to a remote site under endoscopic visualization. To this end, hand-assisted laparoscopic techniques and procedures have been developed. These procedures include both laparoscopic and conventional surgical methodologies. The hand-assisted technique is performed utilizing a seal anchor in conjunction with an access port, which is an enlarged device that protects the incised opening from, for example, infection and contamination.

The maintenance of a substantially fluid-tight seal is desirable to prevent the escape of the insufflation gases and the deflation or collapse of the enlarged surgical site. Accordingly, there is a need for an access assembly used in a hand-assisted minimally invasive procedure that can accommodate a variety of surgical objects while maintaining the integrity of an insufflated workspace.

SUMMARY

In accordance with an embodiment of the present disclosure, there is provided a surgical access assembly including an access port, a seal anchor and a sealing adapter. The access port includes a proximal ring, a distal ring, and a sleeve defining a passage therethrough. The proximal and distal rings are concentrically arranged with the passage of the sleeve. The sleeve extends between the proximal and distal rings. The seal anchor is adapted to be at least partially disposed in the access port. The seal anchor defines a lumen therethrough. The sealing adapter includes a proximal end portion and a distal end portion. The distal end portion is configured and dimensioned to engage the seal anchor in a sealing relation therewith. The proximal end portion is configured and dimensioned to engage a least a portion of the distal ring of the access port in a sealing relation therewith, wherein the sealing adapter is transitionable between a first state in which the sealing adapter has a first diameter and a second state in which the sealing adapter has a second diameter. The second diameter is larger than the first diameter.

In an embodiment, at least one of the proximal and distal end portions of the sealing adapter may include an O-ring. The sealing adapter may include a first inflatable balloon adapted to engage the seal anchor in a sealing relation therewith. In addition, the sealing adapter may include a second inflatable balloon adapted to engage at least a portion of the distal ring of the access port. In particular, the first and second inflatable balloons of the sealing adapter may be concentrically arranged and coplanar with respect to each other. The first and second inflatable balloons may be adapted to be disposed within the distal ring of the access port when positioned in the body cavity. Moreover, the sealing adapter may further include an elongate guide member attached to the first inflatable balloon for manipulation of the first inflatable balloon from a remote position.

The distal ring of the access port may be an O-ring. The proximal ring of the access port may have a kidney-shaped cross-section. The distal ring of the access port may also have a kidney-shaped cross-section. The sleeve of the access port may be rollable about the proximal ring. The seal anchor may include a radially extending flange adapted to engage a portion of the sleeve of the access port in a sealing relation therewith. The proximal and distal rings of the access port may be elastic. The sealing adapter may be made of an elastic material. The seal anchor may be made of a compressible material. The lumen defined in the seal anchor may be dimensioned to receive surgical instruments therethrough.

In accordance with another aspect of the present disclosure, there is provided a method of accessing an internal body cavity. The method includes providing a surgical access assembly including an access port, a seal anchor, and a sealing adapter. In particular, the access port includes a sleeve defining a passage therethrough. The seal anchor is adapted to be at least partially disposed in the access port. The sealing adapter includes proximal and distal end portions. The proximal end portion is configured to engage at least a portion of the access port in a sealing relation therewith. The distal end portion is configured and dimensioned to engage a portion of the seal anchor in a sealing relation therewith. The method further includes positioning the access port at least partially in a body cavity, rolling the sleeve of the access port such that proximal and distal portions of the access port engage an outer epidermal tissue and an internal peritoneal wall of tissue, respectively, positioning the seal anchor at least partially within the access port, and introducing a surgical instrument into the body cavity through the seal anchor.

In an embodiment, the access port may include a proximal ring and a distal ring, wherein the sleeve extends between the proximal and distal rings. The method may further include placing the distal ring of the access port in the sealing adapter adjacent the proximal end portion of the sealing adapter prior to positioning the access port at least partially in the body cavity. The method may further include placing the distal end portion of the sealing adapter into the sleeve of the access port through the distal ring of the access port after placing the distal ring of the access port in the sealing adapter adjacent the proximal end portion of the sealing adapter. Positioning the seal anchor at least partially within the access port may include securely engaging the distal end portion of the sealing adapter disposed in the sleeve of the access port with the seal anchor in a sealing relation therewith.

In an embodiment, the sealing adapter may include a first inflatable balloon adapted to engage the seal anchor in a sealing relation therewith. In addition, the sealing adapter may further include a second inflatable balloon adapted to engage the distal ring of the access port in a sealing relation therewith. The proximal ring of the access port may have a kidney-shaped cross-section. The distal ring of the access port may have a kidney-shaped cross-section adapted to engage a portion of the sealing adapter in a sealing relation therewith. The sleeve may be rollable about the proximal ring. The sealing adapter may be made of elastic material.

The method may further include placing the first and second inflatable balloons of the sealing adapter within the distal ring of the access port. The method may further include removing tissue through the sleeve of the access port. Removing tissue through the sleeve of the access port may include securely engaging the distal portion of the sealing adapter with the proximal ring of the access port. The method may further include insufflating the body cavity.

BRIEF DESCRIPTION OF THE DRAWINGS

Various embodiments of the present disclosure are described hereinbelow with reference to the drawings, wherein.

DETAILED DESCRIPTION OF EMBODIMENTS

Figure 1:
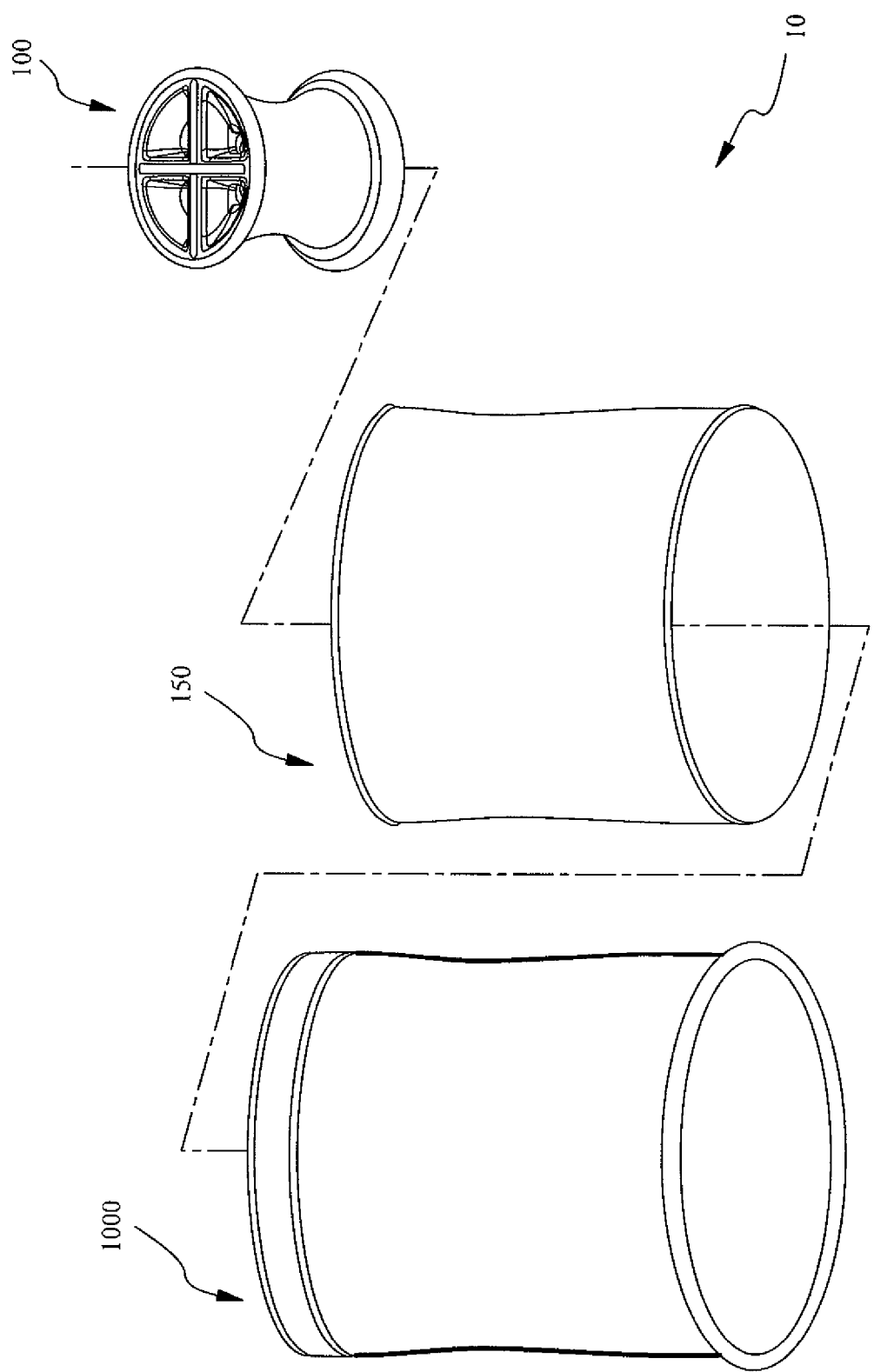
FIG. 1 is a perspective view of a surgical access assembly in accordance with an embodiment of the present disclosure.

Embodiments of the present disclosure will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In the following description, well-known functions or constructions are not described in detail to avoid obscuring the present disclosure in unnecessary detail.

With reference to FIG. 1, there is illustrated a surgical access assembly 10 in accordance with an embodiment of the present disclosure. Surgical access assembly 10 includes a seal anchor 100, a sealing adapter 150, and an access port 1000. Access port 1000 is adapted for insertion within a tissue tract, e.g., through an opening in the abdominal or peritoneal lining, as well as a naturally occurring orifice. Access port 1000 protects the opening from, for example, infection and contamination. In addition, access port 1000 may serve to retract the opening, as will be discussed below. Seal anchor 100 is disposed at least partially within access port 1000. Sealing adapter 150 is configured to engage seal anchor 100 and access port 1000 to provide a substantially fluid-tight seal between a body cavity of a patient and the atmosphere. Both access port 1000 and seal anchor 100, however, may be used as a stand-alone device for insertion of endoscopic instruments.

With continued reference to FIG. 1, seal anchor 100 is configured to receive surgical instruments of varying diameter therethrough. Seal anchor 100 is formed from elastic/compressible type material having sufficient compliance to form a seal about a surgical object and to establish a sealing relation with access port 1000. Furthermore, such material enables seal anchor 100 to accommodate off-axis motion of the surgical object extending therethrough.

Seal anchor 100 contemplates introduction of various types of instrumentation adapted for insertion through a trocar and/or cannula assembly while maintaining a substantially fluid-tight interface about the instrument to help preserve the atmospheric integrity of a surgical workspace from gas and/or fluid leakage. Examples of instrumentation include, but are not limited to, clip appliers, graspers, dissectors, retractors, staplers, laser probes, photographic devices, endoscopes and laparoscopes, tubes, and the like. Such instruments will collectively be referred to as "instruments" or "instrumentation."

Figure 2:
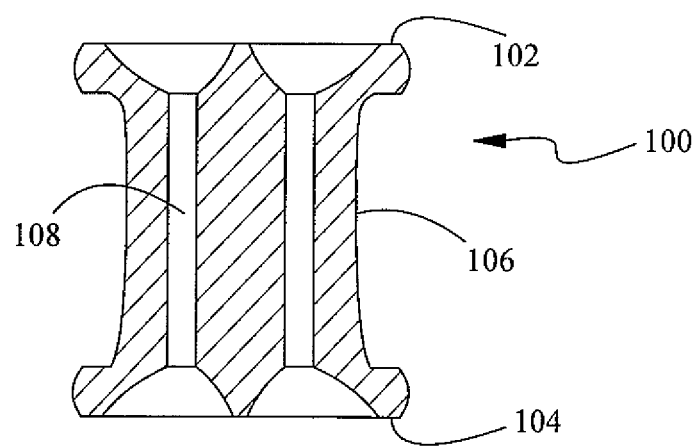
FIG. 2 is a longitudinal cross-sectional view of a seal anchor of the surgical access assembly of FIG. 1.

With reference now to FIG. 2, seal anchor 100 includes proximal and distal end portions 102, 104 and an intermediate portion 106 extending between proximal and distal end portions 102, 104. Seal anchor 100 defines at least one lumen or channel 108 that extends longitudinally between proximal and distal end portions 102, 104. Proximal and distal end portions 102, 104 define substantially planar surfaces. However, proximal and distal end portions 102, 104 may define surfaces that are substantially arcuate to assist in the insertion of seal anchor 100 within tissue. The radial dimension of intermediate portion 106 is appreciably less than those of respective proximal and distal end portions 102, 104. Under such configuration, seal anchor 100 defines an hourglass shape or profile to assist in anchoring seal anchor 100 within tissue when seal anchor 100 is used as a stand-alone device.

Seal anchor 100 is adapted to transition from an expanded condition to a deformed condition to facilitate insertion and securement of the surgical instruments in tissue. Seal anchor 100 is formed of a biocompatible compressible material that facilitates the resilient, reciprocal transitioning of seal anchor 100 between the expanded and deformed conditions thereof. Seal anchor 100 may be biased to the initial condition, and thus in the absence of any force applied to seal anchor 100, seal anchor 100 is in the expanded condition.

Figure 9:
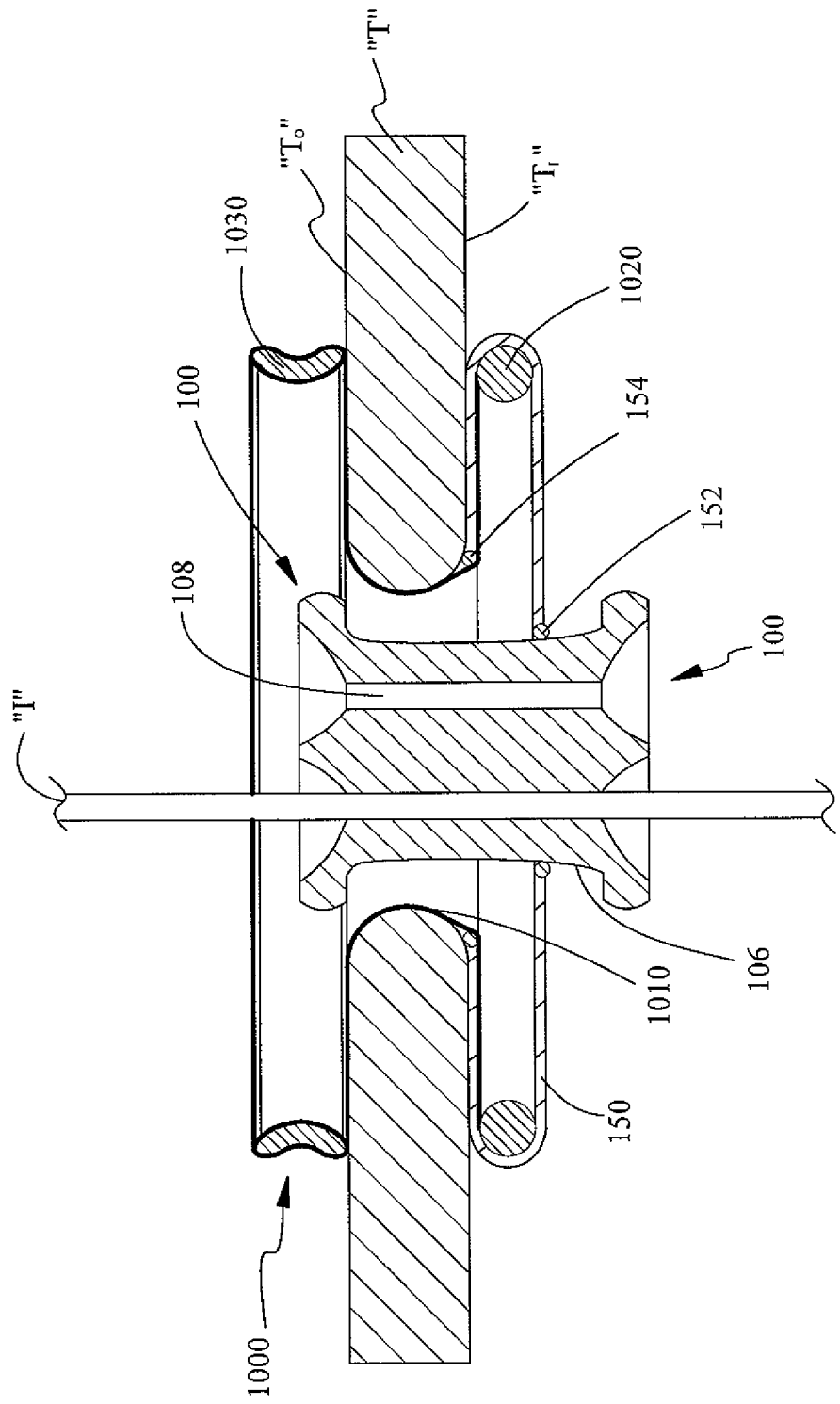

Lumen 108 is configured to removably receive a surgical object "I" (FIG. 9). Lumen 108 may be provided with a built-in valve (not shown) to provide a substantially fluid-tight seal between the body cavity and the atmosphere in the absence of a surgical object "I" in lumen 108 when seal anchor 100 is placed in the opening in tissue "T." Moreover, an access cannula (not shown) having a built-in valve may be utilized to provide a substantially fluid-tight seal between the body cavity and the atmosphere in the absence of surgical objects "I" in the access cannula.

It is also envisioned that prior to the insertion of surgical object "I," lumen 108 may be in a first state in which lumen 108 defines a first or initial dimension that substantially prevents escape of insufflation gas through lumen 108 in the absence of surgical object "I." Upon insertion of surgical object "I" through lumen 108, lumen 108 may transition to a second state in which lumen 108 defines a second, larger dimension that substantially approximates the diameter of surgical object "I" such that a substantially fluid-tight seal is formed with surgical object "I." In particular, the compressible material comprising seal anchor 100 facilitates the resilient transitioning of lumen 108 between its first state and its second state. An example of a seal anchor is disclosed in a commonly assigned U.S. patent application Ser. No. 12/939,204, filed on Nov. 4, 2010, the entire contents of which are fully incorporated herein by reference.

Figure 3:
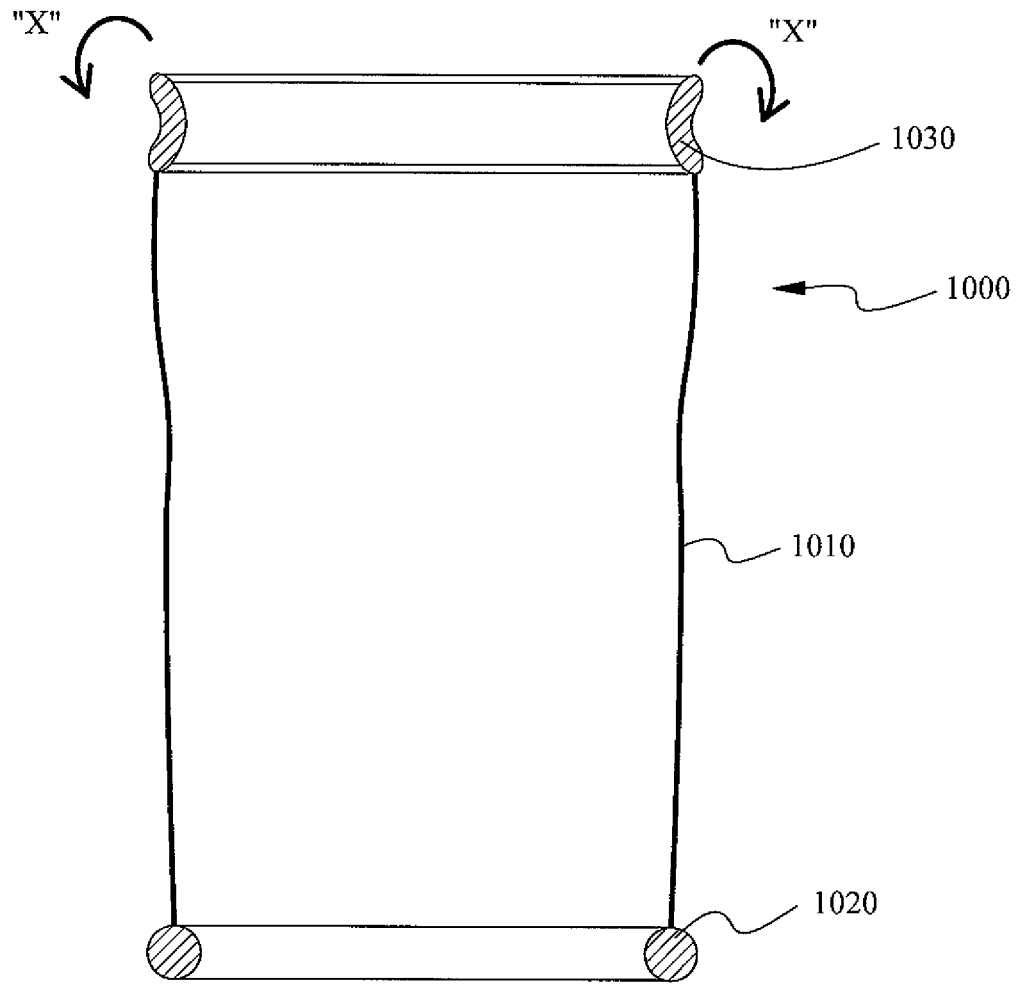
FIG. 3 is a longitudinal cross-sectional view of a seal anchor of the surgical access assembly of FIG. 1.
Figure 8:
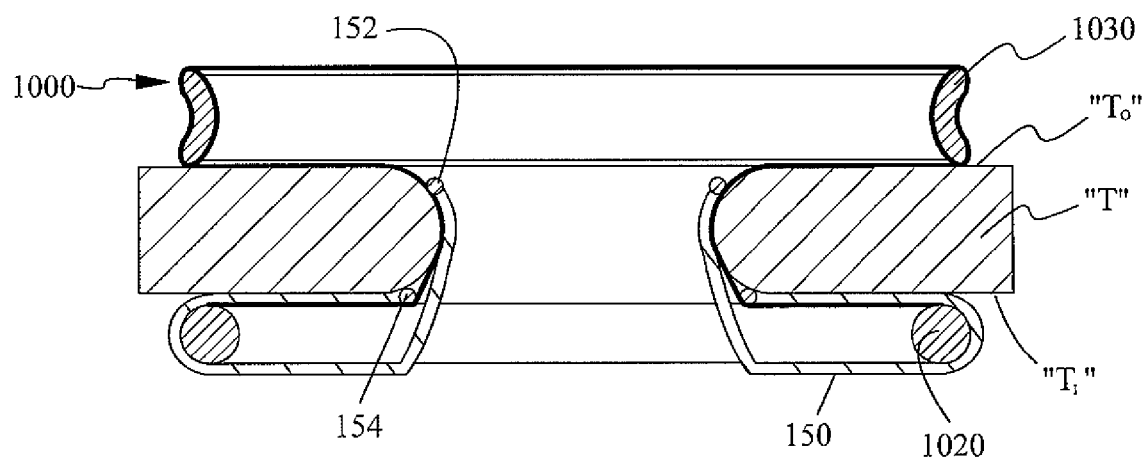

With reference now to FIG. 3, access port 1000 includes a distal ring 1020, a proximal ring 1030, and a flexible sleeve 1010 defining a passage therethrough. Distal and proximal rings 1020, 1030 are concentrically arranged and are longitudinally connected to sleeve 1010. Distal and proximal rings 1020, 1030 are formed of relatively flexible materials to facilitate compression and expansion of distal and proximal rings 1020, 1030. For example, distal and proximal rings 1020, 1030 may be made from an elastomer such as polyurethane, polyethylene, silicone, and the like. The resilient nature of distal and proximal rings 1020, 1030 allows distal and proximal rings 1020, 1030 to return to their normal, substantially annular configuration. In particular, distal and proximal rings 1020, 1030 are adapted to engage the walls defining the body cavity. Distal ring 1020 engages the internal peritoneal wall $T_I$, and proximal ring 1030 engages the outer epidermal tissue $T_O$ (FIG. 8).

Sleeve 1010 has elastomeric properties to facilitate securement of access port 1000 to the opening in tissue "T." Proximal ring 1030 is rollable to gather flexible sleeve 1010 around proximal ring 1030. For example, proximal ring 1030 is rollable, e.g., in the outward direction (as shown by arrow "X" in FIG. 3) to shorten sleeve 1010 and in the inward direction to lengthen the sleeve 1010, or vice versa. Sleeve 1010 may be shortened such that proximal ring 1030 engages the outer epidermal tissue $T_O$ adjacent the opening in tissue "T," and distal ring 1020 positioned in the body cavity engages the internal peritoneal wall $T_I$ (FIG. 8). In this manner, access port 1000 is securely fixed to tissue "T."

With continued reference to FIG. 3, proximal ring 1030 has a kidney-shaped cross-sectional profile. Kidney-shaped cross-section facilitates rolling of sleeve 1010 about proximal ring 1030 and inhibits unrolling of sleeve 1010 over proximal ring 1030 by providing a flattened edge disposed on the outer epidermal tissue $T_O$. Distal rings 1020, on the other hand, is an O-ring having a circular cross-section. However, other cross-sectional profiles are also contemplated for distal and proximal rings 1020, 1030. It is also envisioned that the O-ring may be an inflatable balloon.

In addition, distal and proximal rings 1020, 1030 can vary in size. For example, the dimensions of distal and proximal rings 1020, 1030 may be selectively chosen to be larger than that of a desired opening, as shown in FIG. 8. In this manner, distal and proximal rings 1020, 1030 may have sufficient footing to maintain elastic sleeve 1010 that has been stretched.

By having dimensions of distal and proximal rings 1020, 1030 larger than that of the desired the opening in tissue "T," access port 1000 is adapted to retract/dilate the opening to a desired dimension. More retraction is possible through shortening of sleeve 1010 by rolling proximal ring 1030 outward, in the direction of arrow "X," while less retraction is possible by rolling proximal ring 1030 inward.

Figure 4:
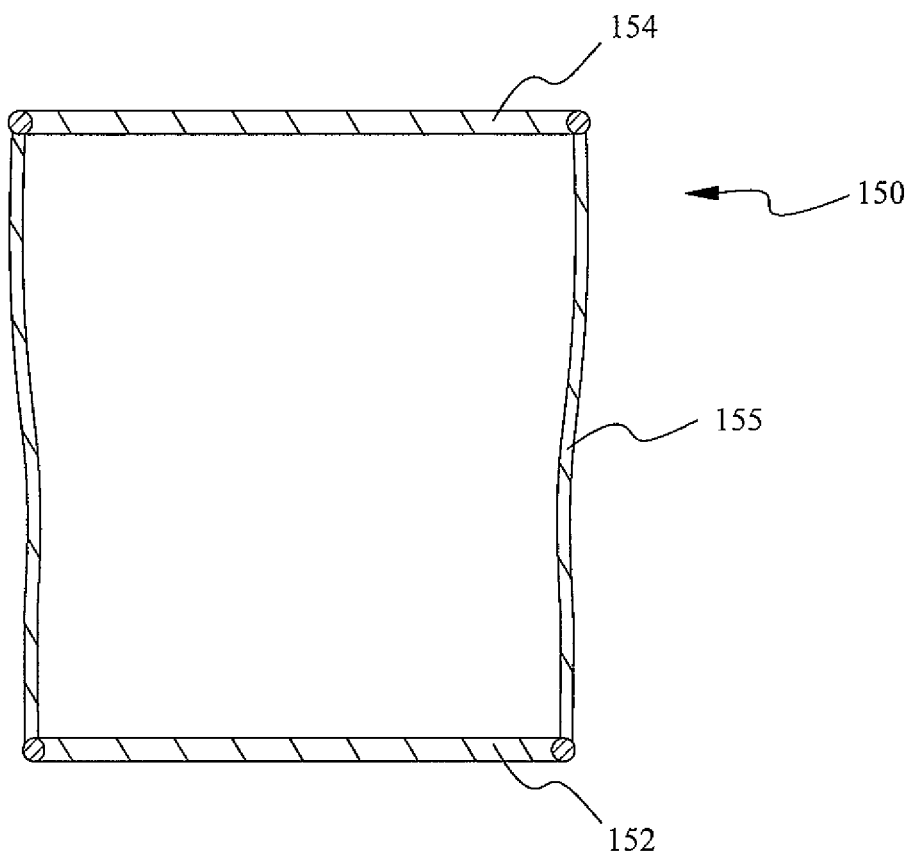
FIG. 4 is a longitudinal cross-sectional view of a sealing adapter of the surgical access assembly of FIG. 1.

With reference now to FIG. 4, sealing adapter 150 is a flexible tubular member having elastomeric properties to facilitate securement with seal anchor 100 and access port 1000 to establish a fluid-tight seal between the body cavity and the atmosphere. Sealing adapter 150 includes distal and proximal end portions 152, 154 and a sleeve 155 that extends between distal and proximal end portions 152, 154. Sleeve 155 defines a passage therethrough. Distal and proximal end portions 152, 154 may include substantially identical construct, characteristics and properties, whereby sealing adapter 150 can be utilized in an inverted manner.

With brief reference to FIG. 9, the flexible nature of sealing adapter 150 enables radial and longitudinal expansion and compression thereof. However, the diameters of distal and proximal end portions 152, 154 of sealing adapter 150 may be tailored to the particular surgical procedure being performed requiring, for example, particular dimensions of the opening in tissue "T." Proximal end portion 154 of sealing adapter 150 is adapted to engage the internal peritoneal wall $T_I$ and flexible sleeve 1010 of access port 1000. On the other hand, distal end portion 152 of sealing adapter 150 is adapted to engage intermediate portion 106 of seal anchor 100 in a sealing relation therewith.

In use, the peritoneal cavity (not shown) is insufflated with a suitable biocompatible gas such as, e.g., $CO_2$ gas, such that the cavity wall is raised and lifted away from the internal organs and tissue housed therein, thereby providing greater access thereto. The insufflation may be performed with an insufflation needle or similar device, as is conventional in the art. Either prior or subsequent to insufflation, an opening is made in tissue "T," the dimensions of which may be varied dependent upon the nature of the procedure.

Figure 5:
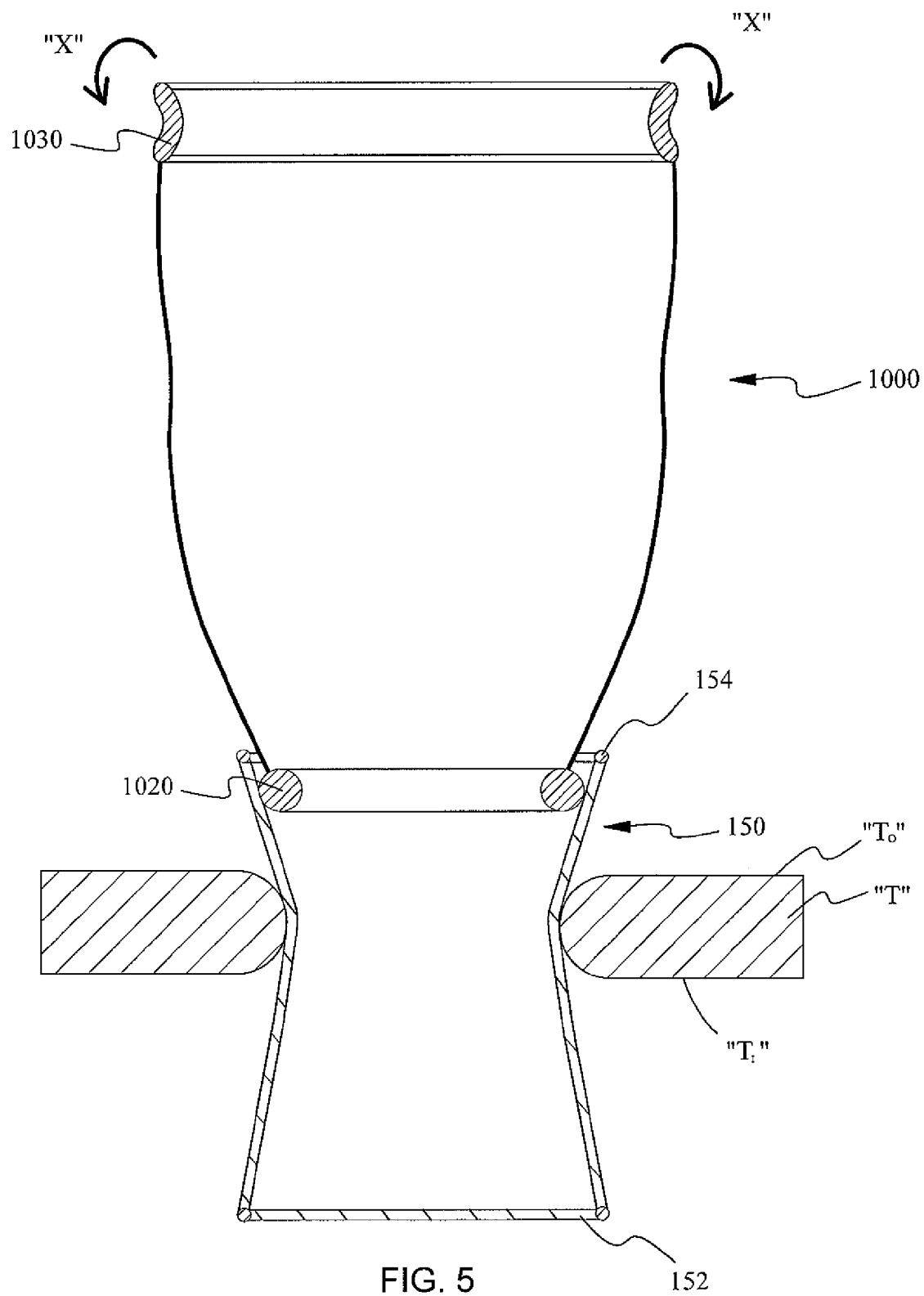
FIGS. 5-9 are longitudinal cross-sectional views of the surgical access assembly of FIG. 1 illustrating a method of use therefor.
Figure 6:
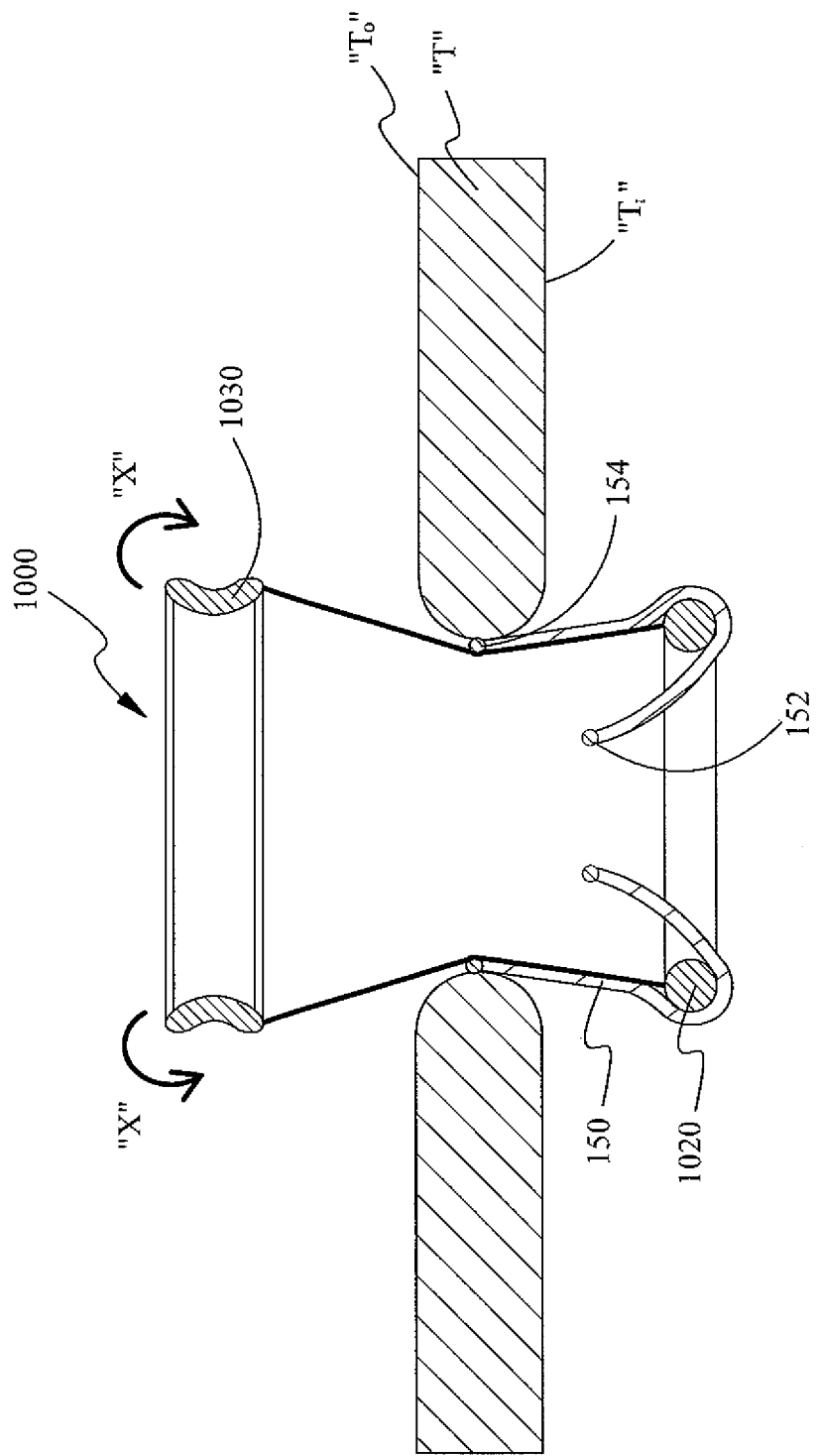

With reference to FIG. 5, prior to the insertion of access port 1000 within tissue "T," distal end portion 152 of sealing adapter 150 is positioned within the body cavity through the opening in tissue "T." In addition, distal ring 1020 of access port 1000 is positioned at least partially within sealing adapter 150 adjacent proximal end portion 154 of sealing adapter 150. Access port 1000 is in its expanded condition, which inhibits the insertion thereof through the opening in tissue "T." To facilitate insertion, the user transitions distal rings 1020 into the compressed condition by, e.g., squeezing distal ring 1020. Compressed distal ring 1020 enclosed by a portion of sealing adapter 150 is inserted through the opening in tissue "T," as shown in FIG. 6. Subsequent to its insertion, distal ring 1020 expands to its expanded state beneath tissue "T." At this time, distal end portion 152 of sealing adapter 150 is pulled proximally through distal ring 1020.

Figure 7:
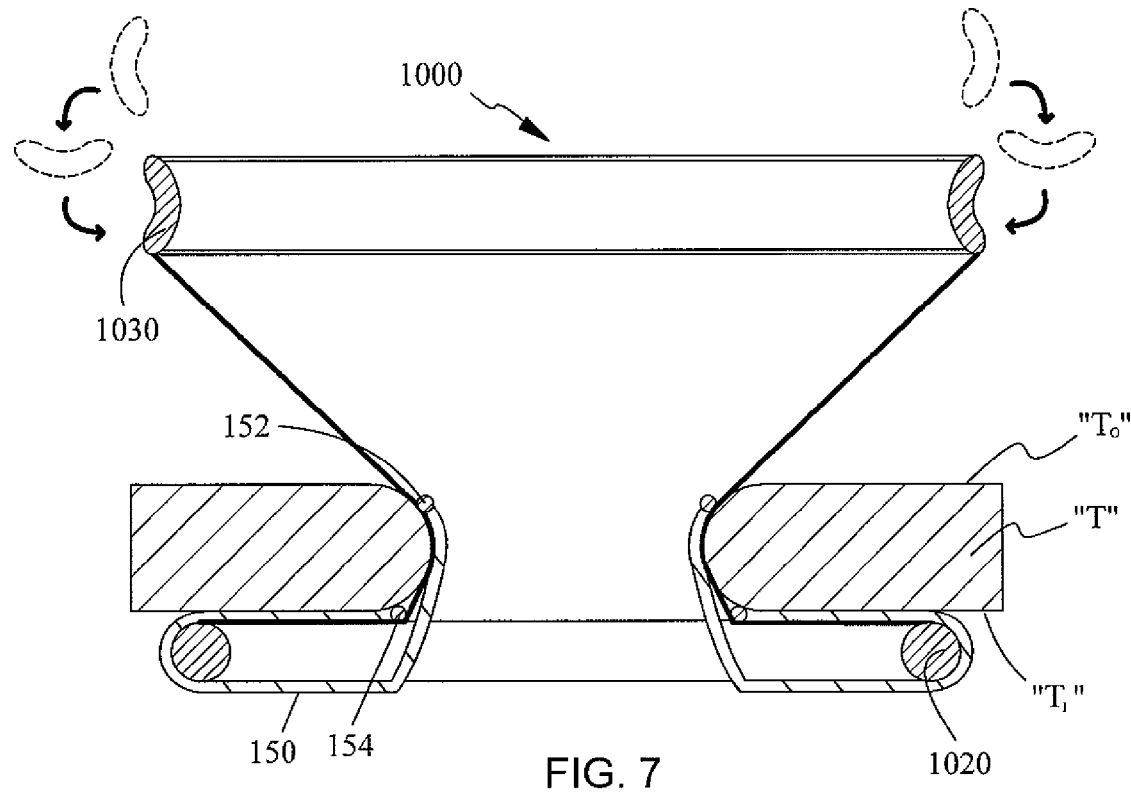

With reference to FIGS. 7 and 8, proximal ring 1030 can be rolled in the direction of arrow "X," as shown in FIG. 5, such that distal ring 1020 causes proximal end portion 154 of sealing adapter 150 to engage the internal peritoneal wall $T_I$, and proximal ring 1030 of access port 1000 engages the outer epidermal tissue $T_O$. In this manner, access port 1000 is securely disposed within the opening in tissue "T," and a portion of sealing adapter 150 is securely fixed between distal ring 1020 of access port 1000 and the internal peritoneal wall $T_I$ of tissue "T." At this time, distal end portion 152 of sealing adapter 150 is disposed within access port 1000 at a position easily accessible to the surgeon. Depending on the nature of the procedure being performed, the opening in tissue "T" may be refracted by further rolling sleeve 1010 about proximal ring 1030.

With reference to FIG. 9, seal anchor 100 can now be disposed at least partially within access port 1000. Distal end portion 152 of sealing adapter 150, which has proximal end portion 154 thereof in a sealing relation with the internal peritoneal wall $T_I$, engages intermediate portion 106 of seal anchor 100 in a fluid-tight seal therewith. In this manner, a fluid-tight seal is established between the body cavity and the atmosphere.

At this time, one or more surgical objects "I" may be inserted through lumen 108 of seal anchor 100. With surgical instruments "I" inserted through lumen 108 and into the body cavity of the patient, the user may swivel or rotate surgical instrument "I" to a desired orientation with respect to tissue "T," while maintaining a fluid-tight seal between a body cavity of a patient and the atmosphere.

During the surgical procedure, surgical instrument "I" and seal anchor 100 may be removed from access port 1000, to enable passage of the surgeon's hand through the opening in tissue "T" to access the body cavity of the patient, if needed. Distal end portion 152 of seal adapter 150 may surround, e.g., the arm of the surgeon, in a fluid-tight seal therewith. Upon completing the surgical procedure, the user may remove the surgical access assembly 10 from the opening of the patient.

Figure 10:
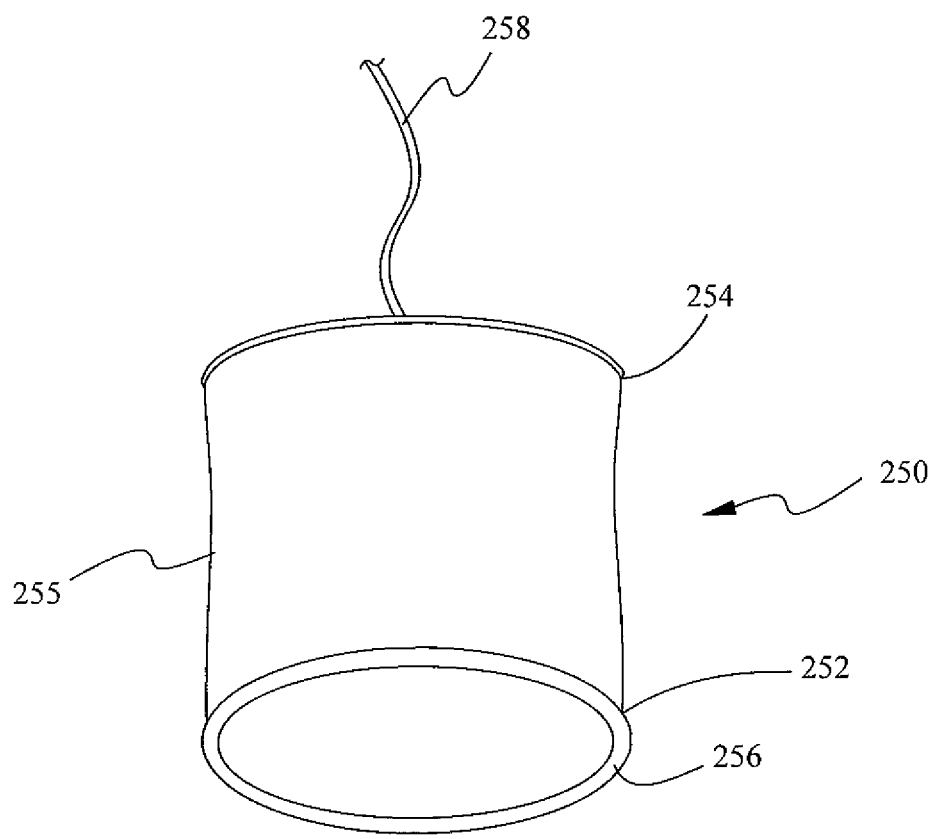
FIG. 10 is a perspective view of another sealing adapter including an inflatable balloon.
Figure 11:
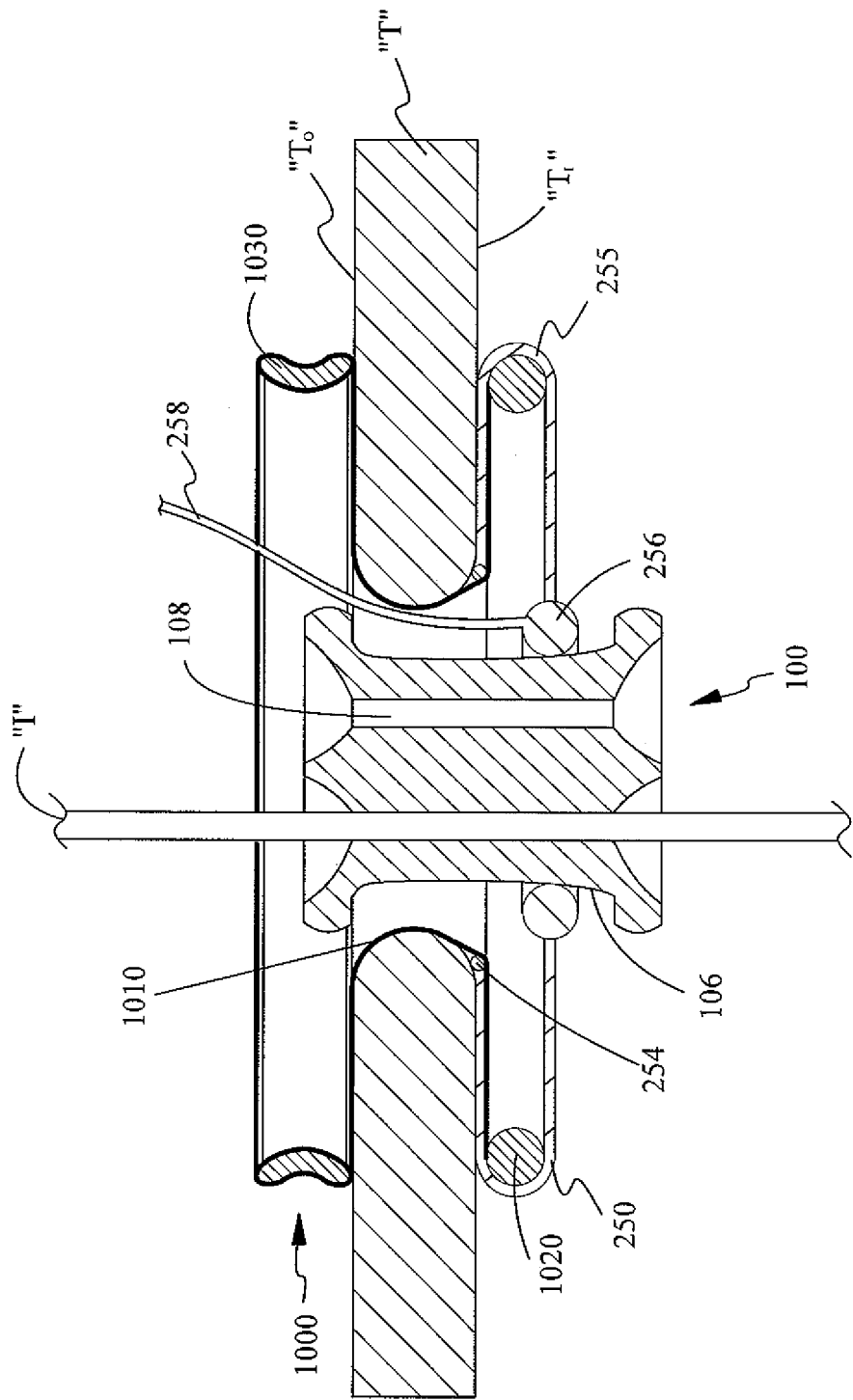
FIG. 11 is a longitudinal cross-sectional view of an access assembly including the sealing adapter of FIG. 10.

With reference now to FIGS. 10 and 11, another embodiment of a seal adapter is illustrated. In the interest of brevity, the present embodiment will focus on the differences between a sealing adapter 250 and the previously described sealing adapter 150. Sealing adapter 250 is a flexible tubular member having elastomeric properties to facilitate securement with seal anchor 100 and access port 1000 to establish a fluid-tight seal between the body cavity and the atmosphere. Sealing adapter 250 includes distal and proximal end portions 252, 254 and a sleeve 255 that extends between distal and proximal end portions 252, 254. In particular, distal end portion 252 includes an inflatable balloon 256 connected to a fluid supply (not shown) through a tube 258.

The flexible nature of sealing adapter 250 enables radial and longitudinal expansion and compression thereof. However, the diameters of distal and proximal end portions 252, 254 may be tailored to the particular surgical procedure being performed requiring, for example, particular dimensions of the opening in tissue "T."

With particular reference to FIG. 11, proximal end portion 254 of sealing adapter 250 is securely supported against the internal peritoneal wall $T_I$ of tissue "T" by distal ring 1020, in conjunction with sleeve 1010 of access port 1000. Inflatable balloon 256 of sealing adapter 250 engages intermediate portion 106 of seal anchor 100. Inflatable balloon 256 is connected to a fluid supply (not shown), wherein upon insertion of inflatable balloon 256 through the opening in tissue "T," the fluid is supplied to inflatable balloon 256 through tube 258 connected to the fluid supply to inflate balloon 256. The inflated balloon 256 establishes a fluid-tight seal against intermediate portion 106 of seal anchor 100. In this manner, sealing adapter 250 establishes a fluid-tight seal between the body cavity and the atmosphere. Fluid can be removed the same way to collapse balloon 256.

Figure 12:
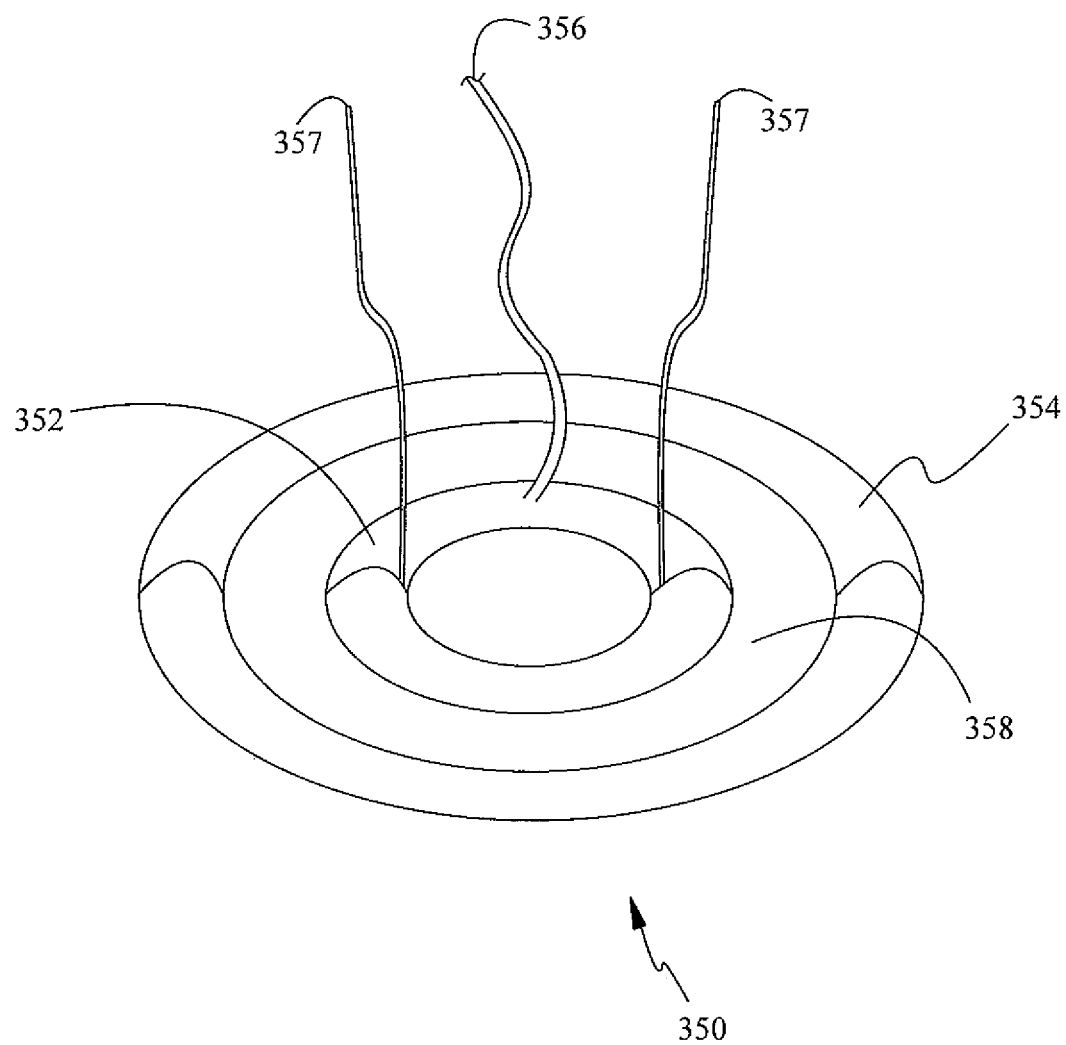
FIG. 12 is a perspective view of another embodiment of a sealing adapter including a pair of inflatable balloons.
Figure 13:
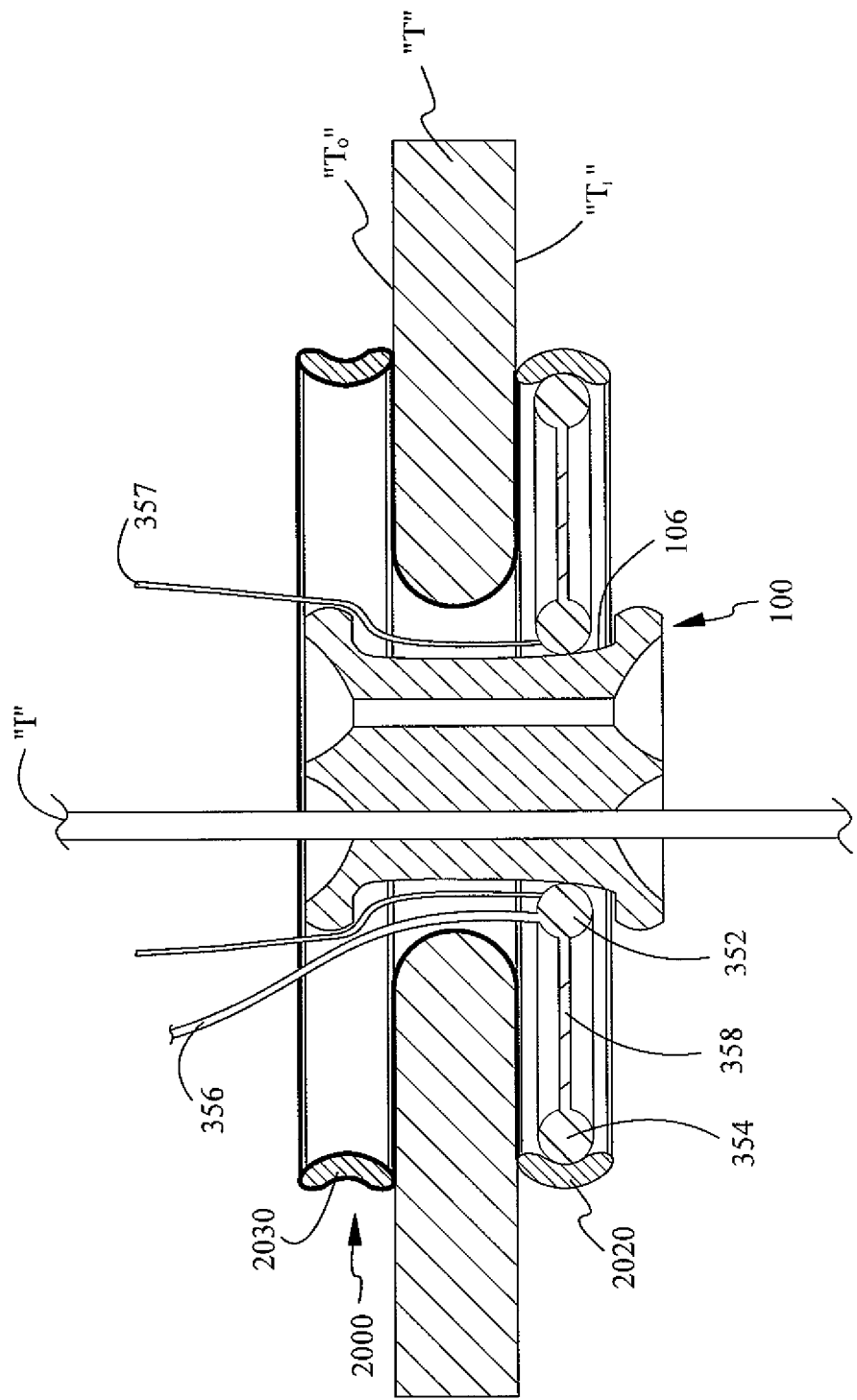
FIG. 13 is a longitudinal cross-sectional view of an access assembly including the sealing adapter of FIG. 12 inserted through the opening in tissue.

With reference now to FIGS. 12 and 13, still another embodiment of a seal adapter is illustrated. In the interest of brevity, the present embodiment will focus on the differences between a sealing adapter 350 and the previously described sealing adapters 150, 250. Sealing adapter 350 is configured to engage intermediate portion 106 of seal anchor 100 and distal ring 2020 of access port 2000 having kidney shaped cross-section in a sealing relation therewith.

Sealing adapter 350 is formed from elastic/compressible type material having sufficient compliance to form a seal with seal anchor 100 and access port 2000. In particular, sealing adapter 350 includes an inflatable inner balloon 352 and an inflatable outer balloon 354. Inflatable inner and outer balloons 352, 354 are in fluid communication through a fluid passage 358. In addition, inner tube 352 is connected to a fluid supply (not shown) through a tube 356. Inflatable inner and outer balloons 352, 354 are concentrically arranged with each other and are coplanar.

With particular reference to FIG. 13, access port 2000 is substantially similar to access port 1000. However, as discussed hereinabove, access port 2000 include distal ring 2020 having a kidney shaped cross-section. In particular, kidney shaped cross-section of distal ring 2020 defines an inward concavity which improves securement and the fluid-tight seal with outer balloon 354 disposed within distal ring 2020.

Sealing adapter 350 may be in a deflated state during insertion through the opening in tissue "T" to facilitate insertion. However, upon placement of sealing adapter 350 within the body cavity, fluid may be supplied through tube 356, whereby inner balloon 352 securely engages intermediate portion 106 of seal anchor 100 in a sealing relation therewith, and outer balloon 354 engages at least an inwardly directed concaved portion of distal ring 2020 of access port 2000. In this manner, sealing adapter 350 is concentrically disposed within distal ring 2020 of access port 2000.

It is further envisioned that sealing adapter 350 may include guide members 357, as shown in FIG. 13, to facilitate positioning of sealing adapter 350 with seal anchor 100 and access port 2000. Guide members 357 are connected to inner ring 352 such that guide members 357 protrude through the opening in tissue "T" without much difficulty. It is further contemplated that tube 356 may be coupled with one of the guide members 357 to reduce entanglement or any other interference with guide members 357.

Figure 14:
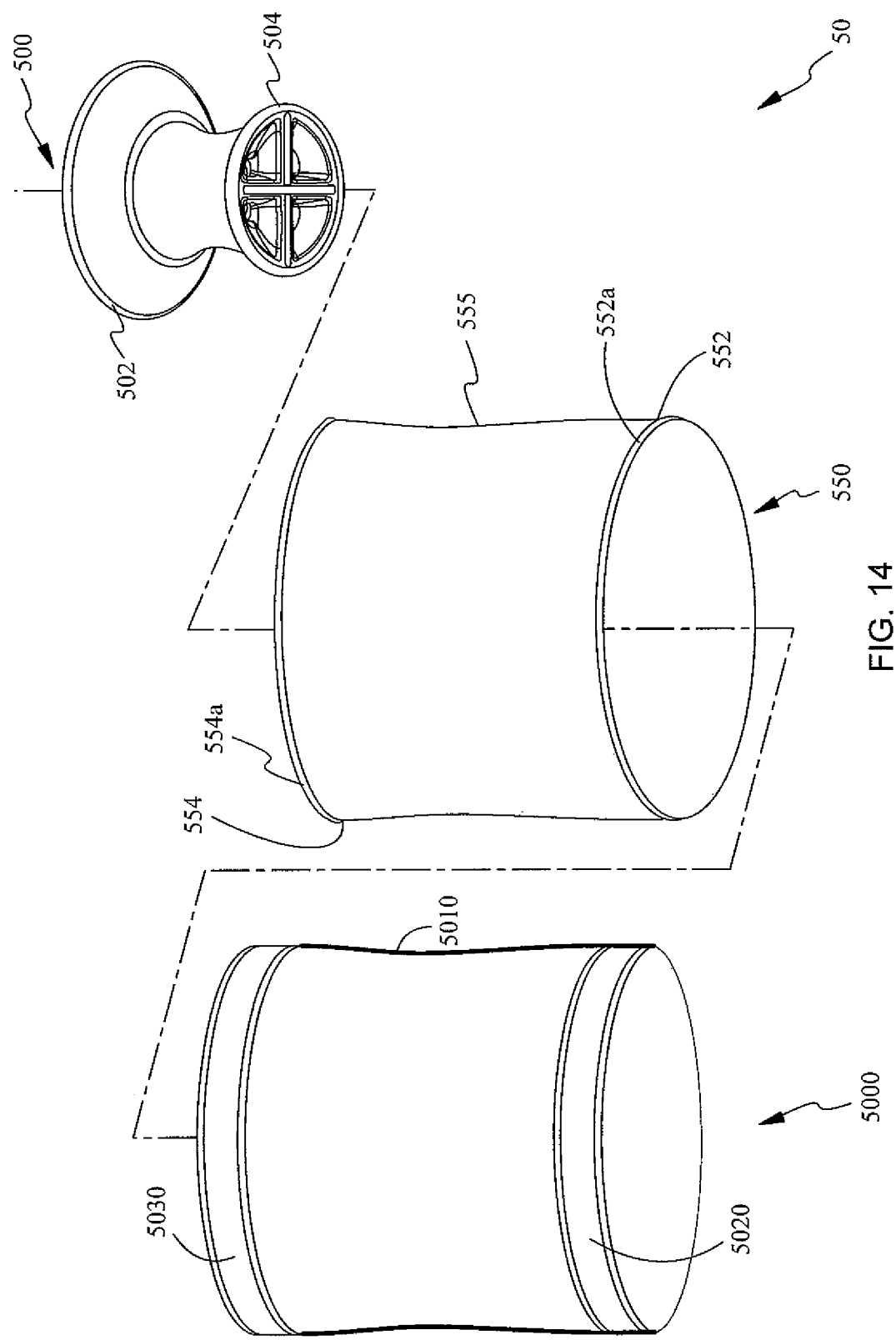
FIG. 14 is a perspective view of another embodiment of an access assembly in accordance with the present disclosure.

In accordance with another embodiment of the present disclosure, access assembly 50 (FIG. 14) is illustrated. In the interest of brevity, the present embodiment will focus on the differences between access assembly 50 and the previously described access assembly 10. With reference to FIG. 14, access assembly 50 includes an access port 5000, seal anchor 500, and a sealing adapter 550. Access port 5000 includes a distal ring 5020, a proximal ring 5030 and a flexible sleeve 5010 defining a passage therethrough. Distal and proximal rings 5020, 5030 are concentrically arranged and are longitudinally connected to sleeve 5010.

In contrast to access port 1000, access port 5000 includes distal and proximal rings 5020, 5030 that both include kidney-shaped cross-section. Kidney-shaped cross-sectional profile of proximal ring 5030 facilitates rolling of sleeve 5010 about proximal ring 5030, and kidney-shaped cross-sectional profile of distal ring 5020 facilitates securement and engagement with sealing adapter 550, as will be discussed hereinbelow. Seal anchor 500 is substantially similar to seal anchor 100. However, a proximal end portion 502 of seal anchor 500 includes a radially extending flange that is substantially larger than that of a distal end portion 504 to facilitate securement of seal anchor 500 in the opening in tissue "T," as will be discussed hereinbelow.

Figure 15:
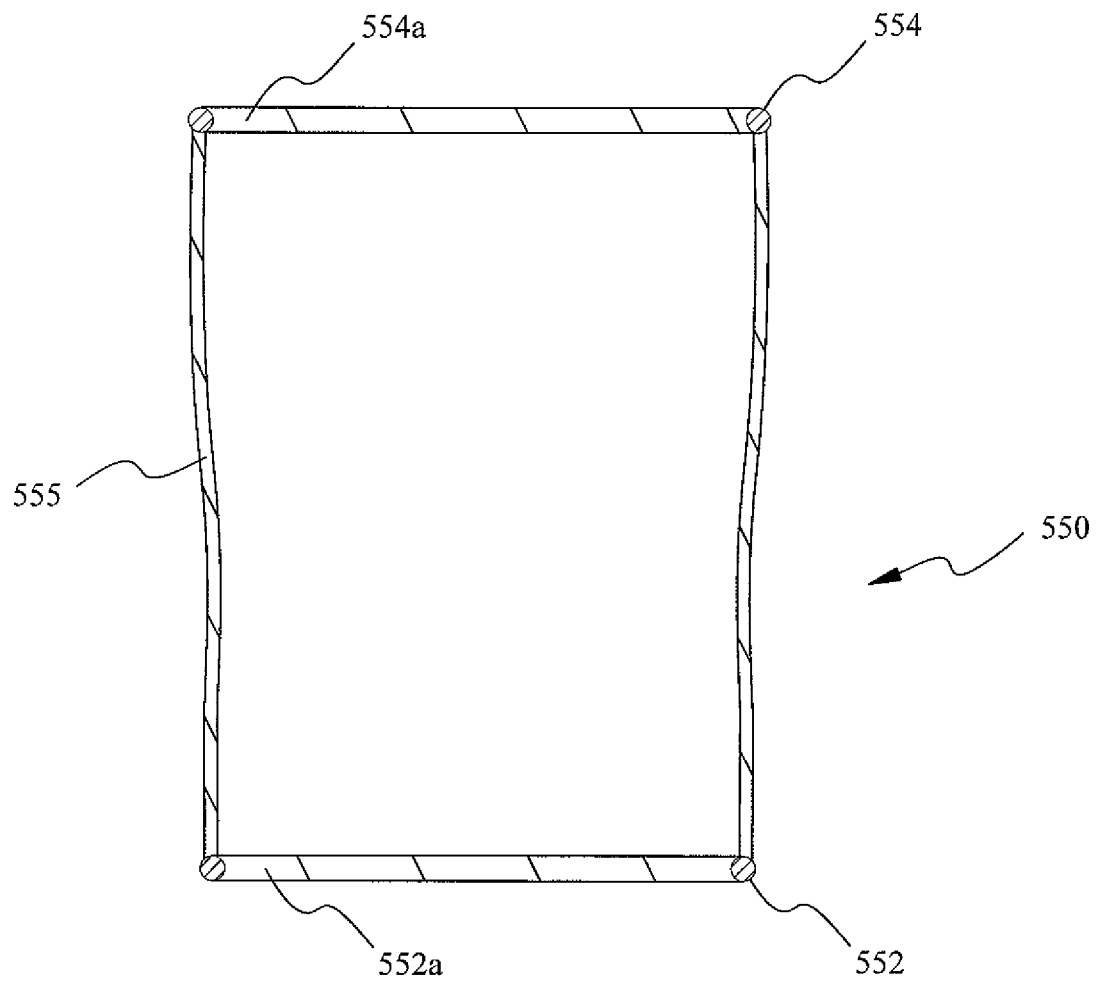
FIG. 15 is a longitudinal cross-sectional view of a sealing adapter of the access assembly of FIG. 14.

With reference now to FIG. 15, sealing adapter 550 is substantially similar to sealing adapter 150. Sealing adapter 550 is a flexible tubular member having elastomeric properties to facilitate securement with seal anchor 500 and access port 5000 to establish a fluid-tight seal between the body cavity and the atmosphere. Sealing adapter 550 includes distal and proximal end portions 552, 554 and a sleeve 555 that extends between distal and proximal end portions 552, 554. Sleeve 555 defines a passage therethrough. However, distal and proximal end portions 552, 554 include distal and proximal rings 552a, 554a, respectively. Distal and proximal rings 552a, 554a may include substantially identical construct, characteristics and properties, whereby distal and proximal rings 552a, 554a can be utilized in an inverted manner. For example, distal and proximal rings 552a, 554a are O-rings.

Figure 16:
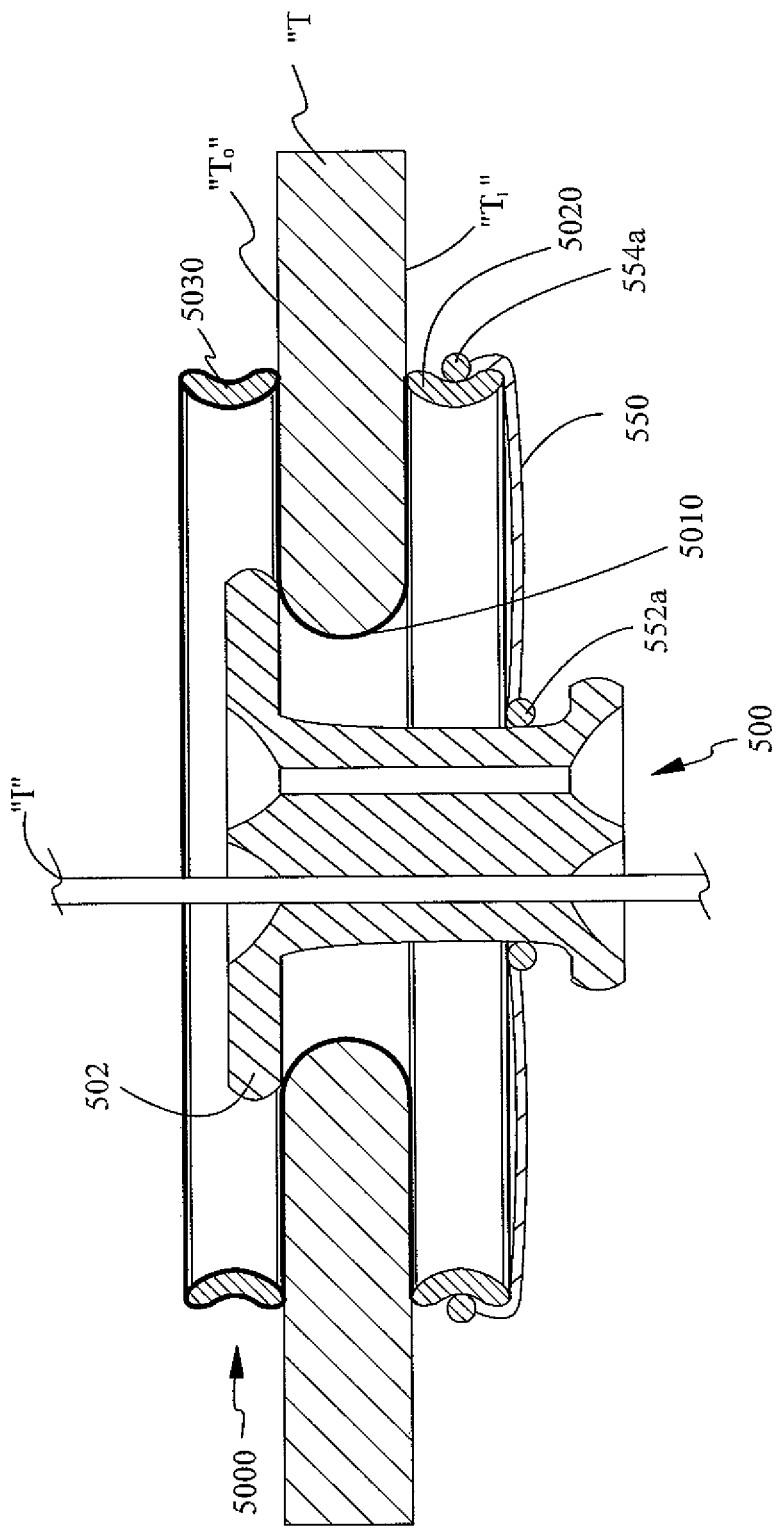
FIG. 16 is a longitudinal cross-sectional view of the access assembly secured to the opening in tissue.

With reference to FIG. 16, proximal end portion 502 of seal anchor 500, which includes a radially extending flange, at least partially engages sleeve 5010 of access port 5000 that engages the outer epidermal tissue $T_O$. Distal ring 5020 of access port 5000 defines a kidney-shaped cross-sectional profile. Proximal ring 554a of sealing adapter 550 securely engages distal ring 5020 of access port 5000, wherein the outwardly directed concaved portion of kidney-shaped cross-section of distal ring 5020 facilitate securement of proximal ring 554a. Distal ring 552a of sealing adapter 550 engages seal anchor 500 in a sealing relation therewith. In this manner, the body cavity is maintained in a fluid-tight seal during a surgical procedure by sealing adapter 550, as well as proximal end portion 502 of seal anchor 500 including a radially extending flange.

Figure 17:
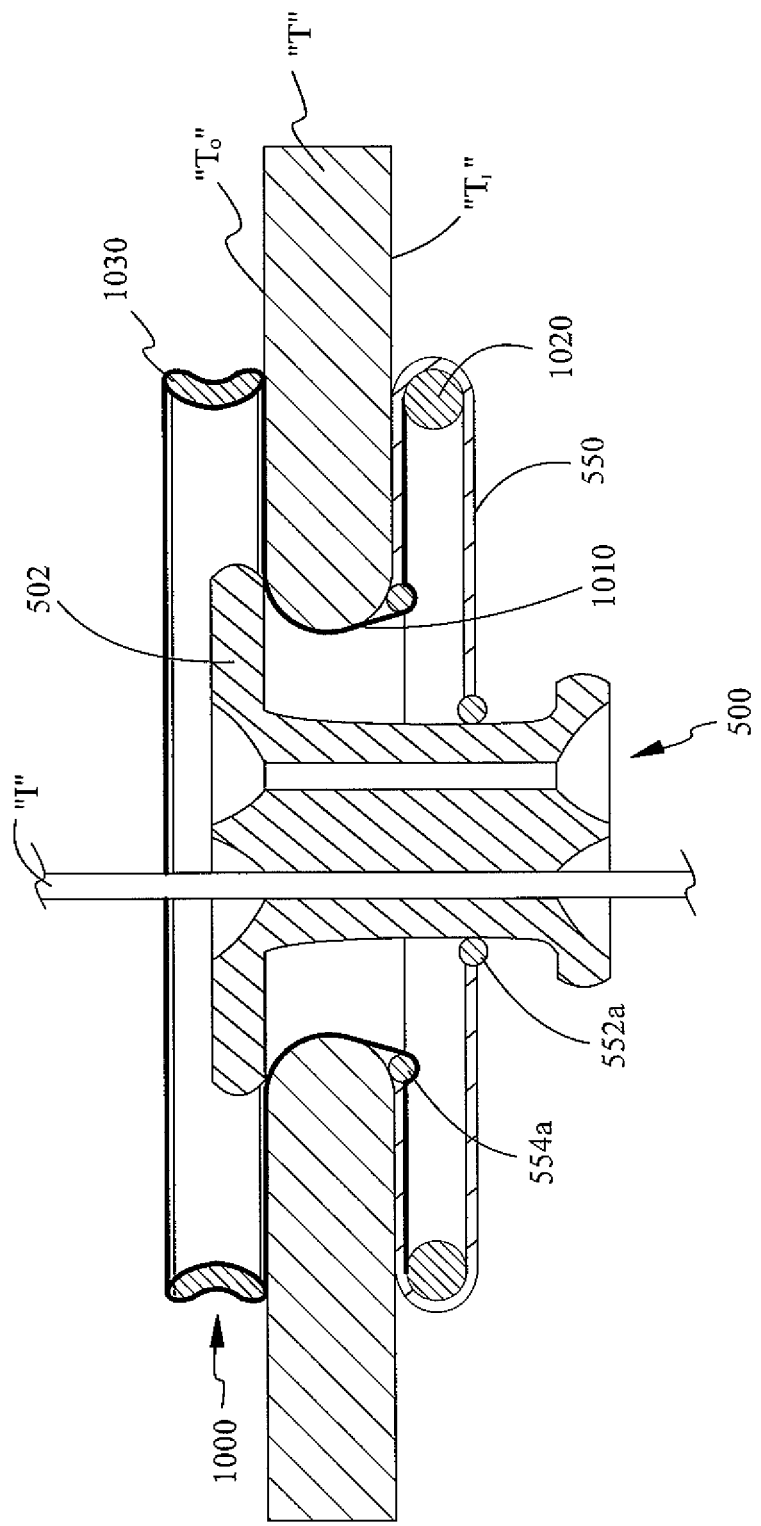
FIG. 17 is a longitudinal cross-sectional view of another embodiment of the access assembly.

With respect to FIG. 17, it is also envisioned that access port 1000 (FIG. 1) can be used with sealing adapter 550 and seal anchor 500. In particular, access port 1000 includes distal ring 1020 such as, for example, an O-ring having a circular cross-section. Under such configuration, proximal ring 554a of sealing anchor 550 securely engages the internal peritoneal wall $T_I$ of tissue "T" supported by distal ring 1020 and sleeve 1010 of access port 1000. Distal ring 552a of sealing adapter 550 is adapted to engage seal anchor 500 in a fluid-tight seal. In this manner, sealing adapter 550 in conjunction with seal anchor 500 including a radially extending flange establishes and maintains a fluid-tight seal between the body cavity and the atmosphere during a surgical procedure.

Figure 18:
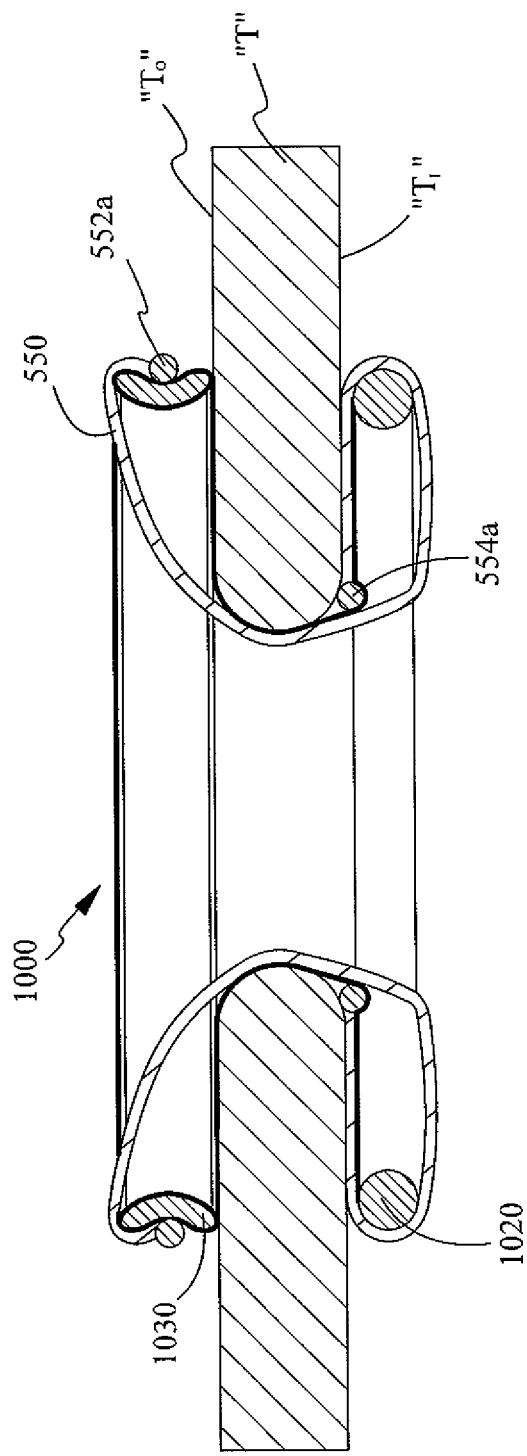
FIG. 18 is a longitudinal cross-sectional view of the access assembly of FIG. 17 illustrating an opening established through the sealing adapter.

The use and operation of the access assembly shown in FIG. 17 is substantially similar to that of access assembly 10 described hereinabove. Thus, the operation and use of the access assembly will not be discussed herein in the interest of brevity. However, it is further contemplated that when seal anchor 500 is not in use, i.e., positioned within the opening in tissue "T," distal ring 552a of sealing adapter 550 may be securely disposed in the outwardly facing concaved portion of kidney-shaped proximal ring 1030 of access port 1000, as shown in FIG. 18. In this manner, an opening is established through sealing adapter 550. At this time, tissue or other organs may be extracted through the opening. However, as seal anchor 500 is repositioned in the opening in tissue "T," a fluid-tight seal may be re-established by engaging distal ring 552a of sealing adapter 550 with seal anchor 500 in a sealing relation therewith.

Although the illustrative embodiments of the present disclosure have been described herein with reference to the accompanying drawings, the above description, disclosure, and figures should not be construed as limiting, but merely as exemplifications of particular embodiments. For example, distal ring 552a of sealing adapter 550 may securely engage seal anchor 500, and proximal ring 554a of sealing adapter 550 may be affixed, e.g., by a biocompatible adhesive, to the outer epidermal tissue $T_O$, whereby proximal ring 1030 of access port 1000 is enclosed by proximal ring 554a of sealing adapter 550. In this manner, sealing adapter 550 establishes a fluid-tight seal between the body cavity and the atmosphere, while accessibly exposed to the atmosphere.

It is to be understood, therefore, that the disclosure is not limited to those precise embodiments, and that various other changes and modifications may be effected therein by one skilled in the art without departing from the scope or spirit of the disclosure.

What is claimed is:

1. A method of accessing a body cavity, comprising:
   providing a surgical access assembly including:
      an access sleeve defining a passage therethrough;
      a seal anchor adapted to be at least partially disposed in the access sleeve; and
      a sealing adapter including first and second end portions, the first end portion configured to engage at least a portion of the access sleeve in a sealing relation therewith, the second end portion configured to engage a portion of the seal anchor in a sealing relation therewith;
   positioning a portion of the access sleeve in the sealing adapter;
   positioning the access sleeve at least partially in the body cavity;
   rolling the access sleeve such that proximal and distal rings of the access sleeve engage tissue;
   positioning the seal anchor at least partially within the access sleeve;
   positioning a portion of the seal anchor within the sealing adapter; and
   introducing a surgical instrument to the body cavity through the seal anchor.

2. The method of accessing the body cavity according to claim 1, wherein positioning the portion of the access sleeve in the sealing adapter includes placing the distal ring of the access sleeve adjacent the first end portion of the sealing adapter.

3. The method of accessing the body cavity according to claim 2, further comprising placing the second end portion of the sealing adapter into the access sleeve through the distal ring after positioning the portion of the access sleeve in the sealing adapter.

4. The method of accessing the body cavity according to claim 3, wherein positioning the portion of the seal anchor within the sealing adapter includes securely engaging the second end portion of the sealing adapter with the seal anchor in a sealing relation.

5. The method of accessing the body cavity according to claim 1, further comprising insufflating the body cavity.

* * * * *